US00PP27943P2

(12) United States Plant Patent
Hartman

(10) Patent No.: US PP27,943 P2
(45) Date of Patent: Apr. 25, 2017

(54) ***CALADIUM* PLANT NAMED 'FRECKLES'**

(50) Latin Name: *Caladium×hortulanum*
Varietal Denomination: Freckles

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 14/998,540

(22) Filed: Jan. 16, 2016

(51) Int. Cl.
*A01H 5/02* (2006.01)

(52) U.S. Cl.
USPC ..... Plt./373

(58) Field of Classification Search
USPC ..... Plt./373
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Caladium* plant named 'Freckles', characterized by its compact, intermediate height, upright and uniformly mounded plant habit; vigorous growth habit and very rapid growth rate; fancy type leaves that are dark green in color with orange and pink-colored spots and blotches; tolerance to full sun conditions; and above average tolerance to *Xanthomonas* Leaf Spot.

4 Drawing Sheets

Botanical designation: *Caladium×hortulanum.*
Cultivar denomination: 'FRECKLES'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Freckles'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2007 in Avon Park, Fla. of *Caladium×hortulanum* 'Twist N' Shout', not patented, as the female, or seed, parent with *Caladium×hortulanum* 'Red Flash', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2008.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2009 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Freckles'. These characteristics in combination distinguish 'Freckles' as a new and distinct *Caladium* plant:

1. Compact, intermediate height, upright and uniformly mounded plant habit.
2. Vigorous growth habit and very rapid growth rate.
3. Fancy type leaves that are dark green in color with orange and pink-colored spots and blotches.
4. Tolerant to full sun conditions.
5. Above average tolerance to *Xanthomonas* Leaf Spot.

Plants of the new *Caladium* differ primarily from plants of the female parent, 'Twist N' Shout', in the following characteristics:

1. Plants of the new *Caladium* have ovate-shaped leaves whereas leaves of 'Twist N' Shout' have hastate-shaped leaves.
2. Leaves of plants of the new *Caladium* are smoother and flatter than leaves of 'Twist N' Shout'.
3. Plants of the new *Caladium* and 'Twist N' Shout' differ in leaf color as leaves of 'Twist N' Shout' are olive green in color with green to coppery bronze-colored venation and coppery orange-colored spots and blotches.

Plants of the new *Caladium* differ primarily from plants of the male parent, 'Red Flash', in the following characteristics:

1. Plants of the new *Caladium* are shorter than plants of 'Red Flash'.
2. Plants of the new *Caladium* are less apically dominant and are denser than plants of 'Red Flash'.
3. Plants of the new *Caladium* and 'Red Flash' differ in leaf color as leaves of 'Red Flash' have red-colored venation and interveinal areas with pink and white-colored spots and dark green-colored borders.
4. Plants of the new *Caladium* and 'Red Flash' differ in leaf petiole color as leaf petioles of 'Red Flash' are reddish pink to tan pink in color with darker-colored stippling, stripes and tessellations.

Plants of the new *Caladium* can be compared to plants of *Caladium×hortulanum* 'Creamsickle', disclosed in U.S. Plant Pat. No. 23,991. In side-by-side comparisons, plants of the new *Caladium* differ primarily from plants of 'Creamsickle' in leaf color as leaves of 'Creamsickle' have greyed green-colored centers and venation with greyed green and greyed purple-colored interveinal areas interspersed with dark green-colored sectors and surrounded by dark green-colored borders. In addition, plants of the new *Caladium* are shorter than plants of 'Creamsickle'.

Plants of the new *Caladium* can be compared to plants of *Caladium×hortulanum* 'Frieda Hemple', not patented. In side-by-side comparisons, plants of the new *Caladium* differ primarily from plants of 'Frieda Hemple' in the following characteristics:

1. Plants of the new *Caladium* are shorter than plants of 'Frieda Hemple'.
2. Plants of the new *Caladium* and 'Frieda Hemple' differ in leaf color as leaves of 'Frieda Hemple' are medium green in color with bright red-colored centers and venation.
3. Plants of the new *Caladium* and 'Frieda Hemple' differ in leaf petiole color as leaf petioles of 'Frieda Hemple' are dark brownish green, close to black, in color.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Freckles' in a container and grown in a shadehouse (tuber not de-eyed).

The photograph at the top of the second sheet is a comparison view of typical potted plants of the female parent, 'Twist N' Shout' (left), 'Freckles' (center) and the male parent, 'Red Flash' (right).

The photograph at the bottom of the second sheet is a comparison view of typical potted plants of 'Creamsickle' (left), 'Freckles' (center) and 'Frieda Hemple' (right).

The photograph at the top of the third sheet is a comparison view of typical plants of 'Freckles' grown in containers; the plant on the left has not had its tuber de-eyed and the plant on the right has had its tuber de-eyed prior to planting.

The photograph at the bottom of the third sheet is a side perspective view of typical plants of 'Freckles' grown in an open field.

The photograph at the top of the fourth sheet is a close-up view of typical freshly-harvested tubers and roots of 'Freckles'.

The photograph at the bottom of the fourth sheet is a close-up view of a typical inflorescence of 'Freckles'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were seven weeks old (vegetative plant photographs and description) and nine weeks old (inflorescence photograph and description), and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Freckles'.

Parentage:

*Female, or seed, parent.*—*Caladium×hortulanum* 'Twist N' Shout', not patented.

*Male, or pollen, parent.*—*Caladium×hortulanum* 'Red Flash', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description (outdoor nursery-grown plants).*—Appearance: Multi-segmented and somewhat flattened; individual segments ovate to irregular in shape. Height: About 3.7 cm. Diameter: About 6 cm to 7.7 cm. Segment height: About 3.3 cm. Segment diameter: About 3.6 cm. Axillary buds, height: About 5 mm. Texture: Thick, starchy; somewhat brittle. Color: Epidermis, freshly-harvested: Close to 159A or close to 159A tinged with close to N170D; outer skin, close to 199A tinged with close to N199A. Epidermis, dried: Close to 200A. Cortical tissue: Close to 10D. Axillary buds: Close to 36B. Root description: Thick, fleshy contractile roots; color, close to 155C. Rooting habit: Medium density.

Plant description:

*Plant type.*—Herbaceous perennial; suitable as a potted plant in containers 15-cm to 25-cm and suitable as a landscape plant in shaded and full sunlight areas.

*Plant and growth habit.*—Intermediate in height, upright and uniformly mounded plant habit; vigorous and dense growth habit; very rapid growth rate; potted plants in finished or saleable form in about seven weeks after planting tubers; leaf petioles and leaves arise from one or more growing points on tubers; petioles mostly upright and curving outwardly with development.

*Plant height, from soil level to top of foliar plane, shadehouse-grown potted plants.*—About 31 cm to 40 cm.

*Plant height, from soil level to top of inflorescences, shadehouse-grown potted plants.*—About 42.5 cm.

*Plant diameter or spread, shadehouse-grown potted plants.*—About 33 cm to 45 cm.

*Number of shoots per plant, shadehouse-grown potted plants, tubers not de-eyed.*—About two develop per #1 tuber.

*Number of shoots per plant, shadehouse-grown potted plants, tubers de-eyed*.—About three to four develop per #1 tuber.

*Cataphylls, shadehouse-grown potted plants*.—Length: About 6 cm to 9 cm. Width: About 1.5 cm to 2.2 cm. Shape: Wedge-shaped. Apex: Acute to cuspidate. Base: Sheathing the stem. Color, inner surface: Close to 194D; colors and patterns on the outer surface are visible on the inner surface. Color, outer surface: Close to between 156C and 195C, variably tinged with close to 182D and 147A and stippled, streaked and tessellated with close to 199A to 200A tinged with close to 147A; with development, color becoming closer to 200A to 200B and 200C stained with close to 187C.

Leaf description:

*Arrangement and type*.—Alternate; simple; fancy-type.

*Length, shadehouse-grown potted plants*.—About 21 cm to 30 cm.

*Width, shadehouse-grown potted plants, flattened*.—About 13 cm to 18.8 cm.

*Shape*.—Ovate.

*Apex*.—Acute to acuminate.

*Base*.—Sagittate to peltate.

*Margin*.—Entire; wavy with broad undulations.

*Texture, upper and lower surfaces*.—Smooth, glabrous.

*Luster, upper surface*.—Dull sheen; immature leaves with somewhat metallic sheen.

*Luster, lower surface*.—Glaucous, dull sheen.

*Venation pattern*.—Pinnate.

*Color, shadehouse-grown potted plants*.—Developing leaves, upper surface: Ground color: Darker and more green than 139A tinged with close to 147A. Midvein and primary veins: Darker than 139A tinged with close to 147A. Interveinal areas: Large blotches, close to 47A and close to 47A tinged with close to 48A; spots, close to 49A and 49B typically surrounded with close to 194B to 194C. Leaf petiole attachment site and adjacent areas: Close to N186A. Margins: Thin margin, close to 187A. Basal notch: Close to N187C. Developing leaves, lower surface: Ground color: Close to 191A and close to 191A tinged with close to 189A. Midvein and primary veins: Close to 194B tinged with close to 160C. Secondary veins: Close to 191A tinged with close to 189A surrounded with close to 193A. Interveinal areas: Large blotches, close to 49B, close to 179D tinged with close to 194D, close to 37C and close to 37C tinged with close to 194D; spots, close to 49C and close to 49D tinged with close to 194D. Leaf petiole attachment site and adjacent area: Tinged with close to 187C. Margins: Thin margin, close to 187A. Basal notch: Close to 187A. Fully expanded leaves, upper surface: Ground color: Darker and more green than 139A tinged with close to 137A. Midvein and primary veins: Darker than 139A tinged with close to 137A. Interveinal areas: Large blotches, close to 47A, close to 47A tinged with close to 48A and close to 179A; spots, close to 49A and 49B typically surrounded with close to 194C. Leaf petiole attachment site and adjacent areas: Close to N186A. Margins: Thin margin, close to 187A. Basal notch: Close to N187C. Fully expanded leaves, lower surface: Ground color: Close to 191A. Midvein and primary veins: Close to 195B tinged with close to 160C. Secondary veins: Close to 191A tinged with close to 189A surrounded with close to 193A. Interveinal areas: Large blotches, close to 37C, close to 37C tinged with close to 194C and close to 179D tinged with close to 194C; spots, close to 49C and close to 49D tinged with close to 194D. Leaf petiole attachment site and adjacent area: Tinged with close to 187C. Margins: Thin margin, close to 187A. Basal notch: Close to 187A.

*Petioles*.—Aspect: Initially upright and straight; with development, curving outwardly; flexible. Length, shadehouse-grown potted plants: About 24 cm to 35 cm. Diameter, distally, shadehouse-grown potted plants: About 4.5 mm to 6 mm. Diameter, proximally, shadehouse-grown potted plants: About 7 mm to 12 mm. Texture: Smooth, glabrous; glaucous. Color, shadehouse-grown potted plants: Close to 195A variable tinged with close to 182D, stippled, streaked and tessellated with close to 199A and close to 200A tinged with close to 147B; below the leaf and petiole junction, close to 195A or close to 195B faintly tinged with close to 182D, variably and faintly stippled, streaked and tessellated with close to N199A. Wing length, shadehouse-grown potted plants: About 4.7 cm to 8 cm. Wing diameter, shadehouse-grown potted plants: About 1 cm. Texture, inner and outer surfaces: Smooth, glabrous. Luster, inner and outer surfaces: Dull to slightly glossy. Wing color, shadehouse-grown potted plants: Inner surface: Close to 194D; colors and patterns on the outer surface are visible on the inner surface. Outer surface: Close to 156C and close to 195C variably tinged with close to 182D and 147A, stippled, streaked and tessellated with close to 199A and 200A tinged with close to 147B.

Inflorescence description: Inflorescences observed on nine week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; sweet, jasmine-like with camphor note.

*Natural flowering season and flower longevity*.—Plants of the new *Caladium* typically flower during the spring and summer in central Florida; flowers develop about nine weeks after growth commences; inflorescences last about three days before fading; inflorescences persistent.

*Spathe*.—Length, overall: About 12 cm. Length, distal open portion: About 8 cm. Length, proximal closed portion: About 4 cm. Width, distal open portion: About 5 cm. Depth, distal open portion: About 2.4 cm. Width, at constriction: About 1.4 cm. Width, proximal closed portion: About 2.6 cm. Shape: Elliptic to slightly obovate. Apex: Acuminate. Base: Obtuse, tapered. Margin: Entire; flat to slightly recurved. Texture, front and rear surfaces: Smooth, glabrous. Luster, front surface: Dull sheen. Luster, rear surface: Slightly glaucous, dull sheen. Color, front surface: Distal open portion: Close to 155C and close to 157A with sparse fine speckles or spots, close to 47A or close to 179A; with development, color becoming closer to 199A. Proximal closed portion: Overall, close to 148D; proximally streaked and flushed with close to 187A and 187B; color does not change with development. Color, rear surface: Distal open portion: Close to 157D flushed with close to 145C and 145D; color does not change with development. Proximal closed portion: Close to 147B and close to 147C tinged with close to 146D; color does not change with development.

*Spadix*.—Length, overall: About 10.6 cm. Length, male flower zone: About 5.5 cm. Length, sterile zone: About 3.1 cm. Length, female flower zone: About 2 cm. Diameter, male flower zone: About 1 cm. Diameter, sterile flower zone: About 6.5 mm. Diameter, female flower zone: About 1.1 cm. Shape: Columnar. Apex: Acute. Base: Obtuse. Aspect: Upright. Color, mature, male zone: Close to 155B. Color, mature, sterile zone: Close to 155B. Color, mature, female zone: Close to 8D and 159D. Male flowers: Quantity per spadix: About 160. Shape: Obovate. Height: About 3 mm. Diameter: About 4 mm. Pollen amount: Moderate. Pollen color: Close to 4C to 4D. Female flowers: Quantity per spadix: About 190. Shape: Ovate. Height: About 2.5 mm. Diameter: About 2 mm. Stigma color: Close to 155D. Ovary color: Close to 8D and 159D.

*Scape*.—Length: About 30.5 cm. Diameter: About 6.5 mm. Strength: Sturdy; flexible. Aspect: Mostly erect. Texture: Smooth, glabrous. Luster: Dull sheen; glaucous. Color: Close to 147B tinged with close to 148B; stippled and streaked with close to 199A; just below spathe, close to 146B tinged with close to 147B.

*Seeds and fruits*.—To date, seed and fruit development have not been observed on plants of the new *Caladium*.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment overwinter for re-planting the following spring.

It is claimed:

1. A new and distinct *Caladium* plant named 'Freckles' as illustrated and described.

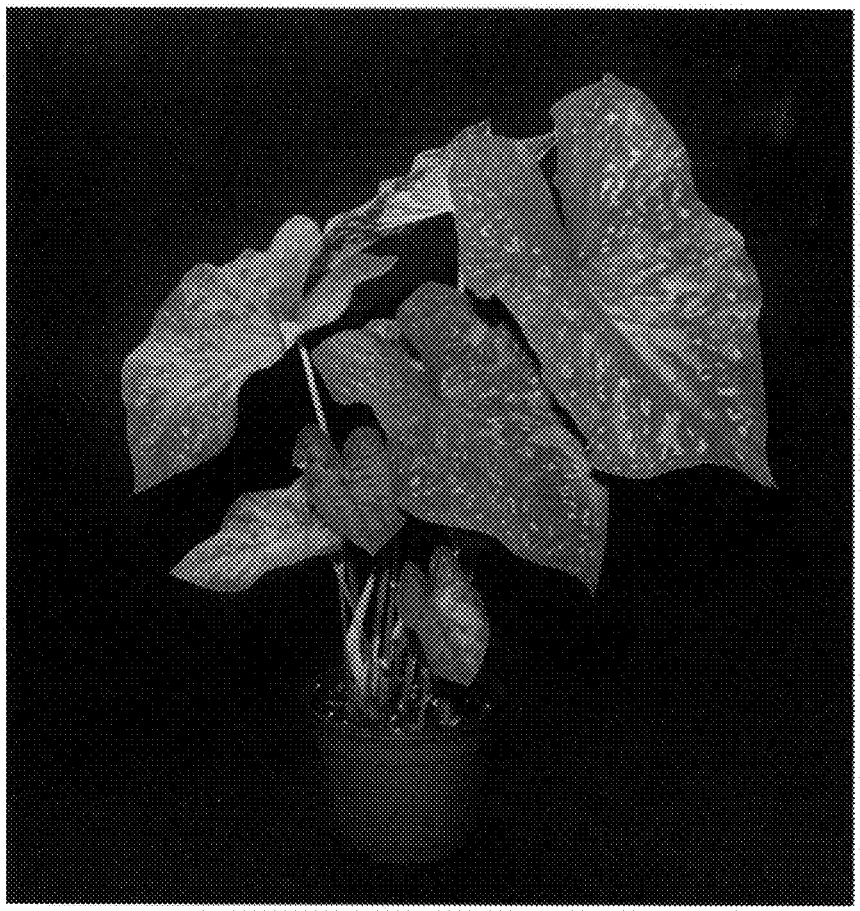

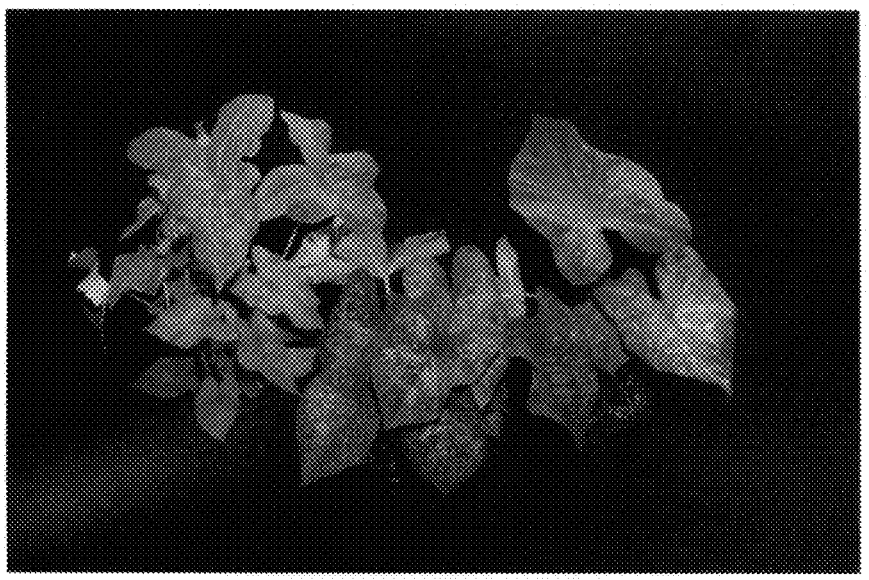
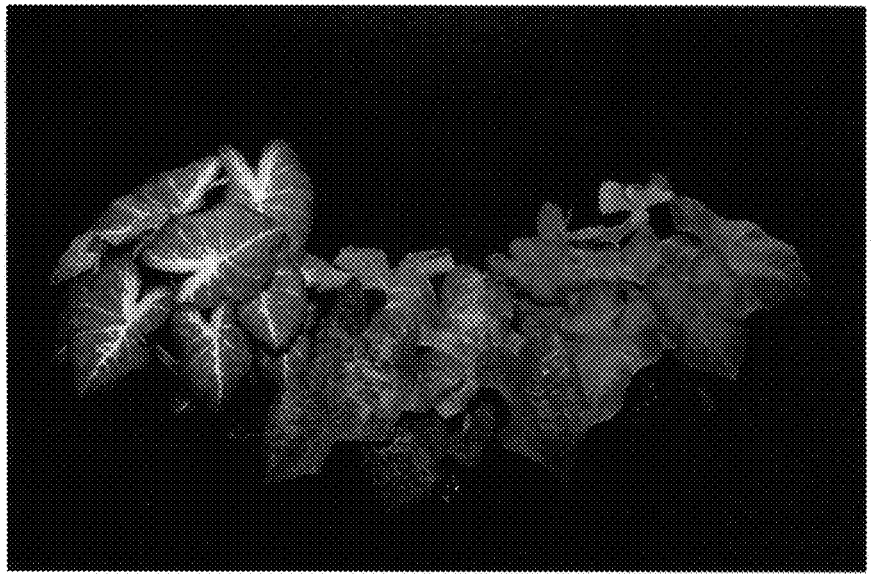

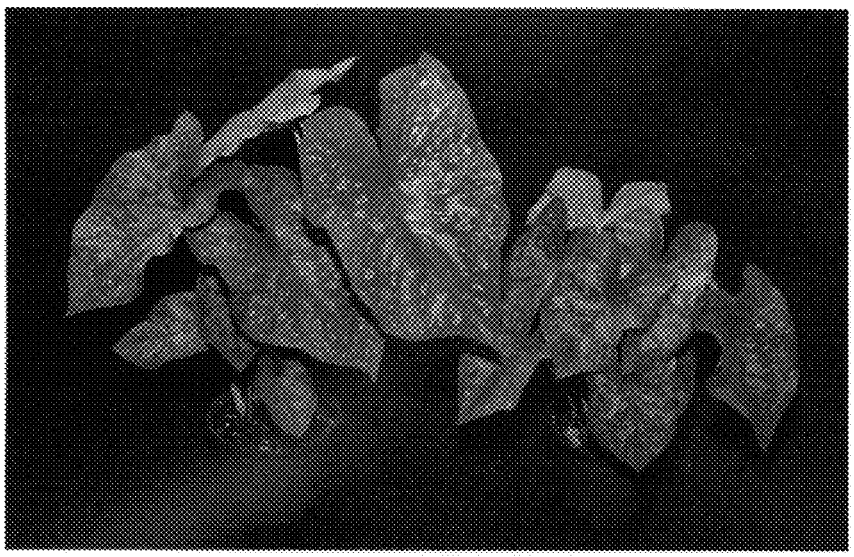
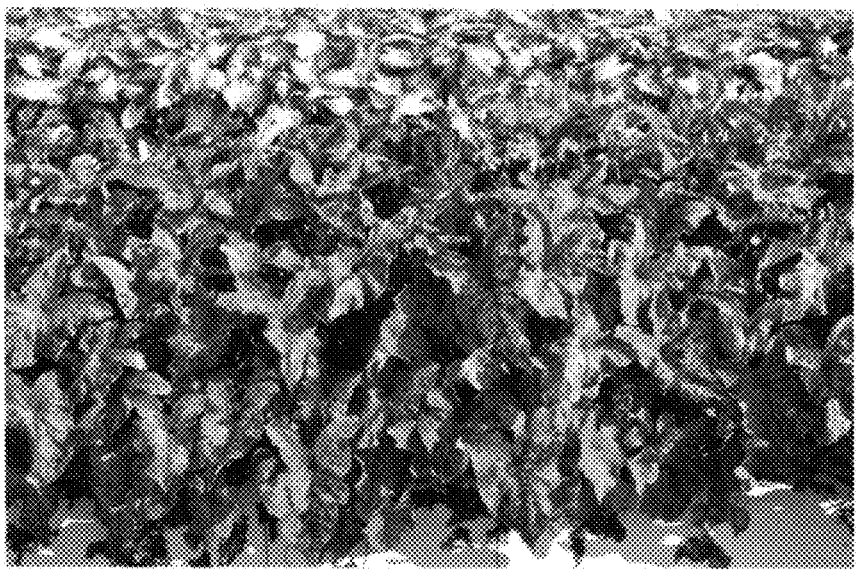

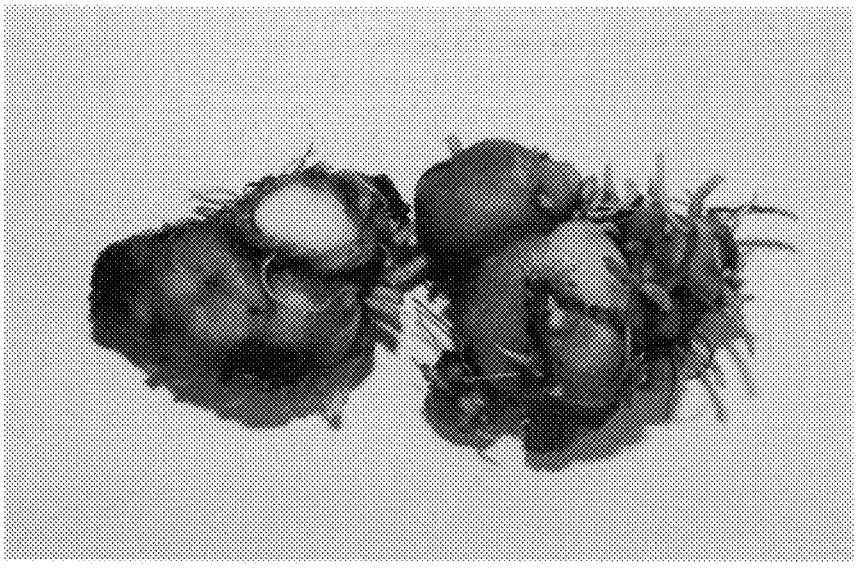
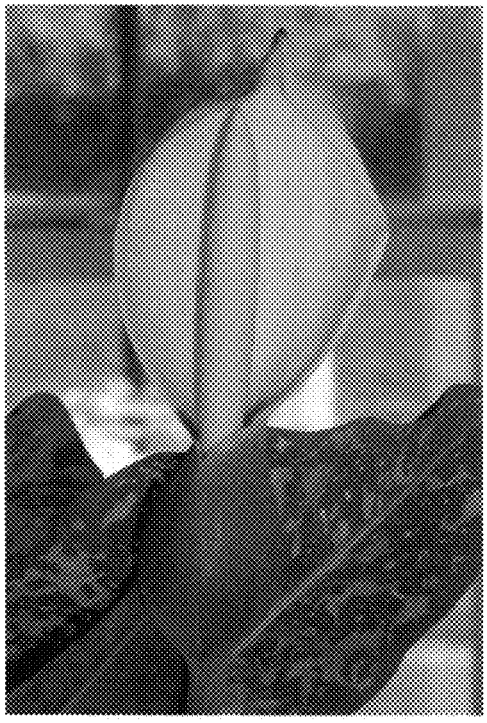

* * * * *